United States Patent [19]

Nygard et al.

[11] Patent Number: 5,758,651
[45] Date of Patent: Jun. 2, 1998

[54] TELEMETRY SYSTEM AND APPARATUS

[76] Inventors: Tony Mikeal Nygard, 14 Stacey Close, Kariong, N.S.W. 2250; Chris Newton Daly, 95 Beryl Crescent, Bilgoa Plateau, N.S.W. 2107; Jim Finlay Patrick, 5 Arding Street, Lane Cove, N.S.W. 2066; David Kerry Money, 50 Blackbutt Avenue, Pennant Hills, N.S.W. 2120, all of Australia

[21] Appl. No.: 454,263
[22] PCT Filed: Dec. 22, 1993
[86] PCT No.: PCT/AU93/00670
    § 371 Date: Jun. 13, 1995
    § 102(e) Date: Jun. 13, 1995
[87] PCT Pub. No.: WO94/14376
    PCT Pub. Date: Jul. 7, 1994

[30] Foreign Application Priority Data

Dec. 22, 1992 [AU] Australia .................... PL6522

[51] Int. Cl.$^6$ ........................... A61N 1/04
[52] U.S. Cl. ............ 128/741; 128/746; 607/55; 607/57; 607/133
[58] Field of Search .............. 607/137, 57, 59, 607/60, 111, 55, 56; 128/642, 746, 741; 600/25

[56] References Cited

U.S. PATENT DOCUMENTS

| | | | |
|---|---|---|---|
| 4,535,785 | 8/1985 | van den Honert et al. | 128/746 |
| 4,570,640 | 2/1986 | Barsa | 128/741 |
| 4,819,647 | 4/1989 | Byers et al. | 607/116 |
| 5,123,422 | 6/1992 | Charvin | 607/137 |
| 5,569,307 | 10/1996 | Schulman et al. | 607/55 |

FOREIGN PATENT DOCUMENTS

| | | |
|---|---|---|
| 569636 | 3/1986 | Australia . |
| 0124930 | 11/1984 | European Pat. Off. . |
| 0214527 | 3/1987 | European Pat. Off. . |
| 0241101 | 10/1987 | European Pat. Off. . |
| 0247649 | 12/1987 | European Pat. Off. . |
| 2124495 | 2/1984 | United Kingdom . |

OTHER PUBLICATIONS

Proceedings of the Ninth Annual Conference of the IEEE Engineering in Medicine and Biology Society, F.A. Spellman et al. 11/16/7, Boston (US), vol. 4 of 4, p. 1911–1912.

Primary Examiner—Robert L. Nasser
Attorney, Agent, or Firm—Gottlieb, Rackman & Reisman

[57] ABSTRACT

A system is disclosed for enabling telemetry from an auditory prosthesis, illustratively a cochlear prosthesis. An electrode array 10 is used both for delivering electrical stimuli, and for sensing evoked potentials. Preferably a delay is provided between stimulus and measurement, and the sensing electrodes are distinct from the stimulus electrodes.

11 Claims, 4 Drawing Sheets

Note: INTERNAL TO IMPLANT

TELEMETRY SYSTEM AND APPARATUS

FIELD OF THE INVENTION

This invention relates to a telemetry system and apparatus for recovering data from an auditory prosthesis.

BACKGROUND ART

After an auditory prosthesis, such as a cochlear prosthesis, is surgically implanted, it is advantageous if data can be obtained about the actual performance of the electrode array, and the response of the auditory nerve to stimulation. This enables detection or confirmation of normal operation of the device, and optimisation of stimulus parameters in an objective fashion. Similar requirements apply to other implanted auditory prostheses.

It is an object of the present invention to provide a telemetry system for an auditory prosthesis such that the required data may be effectively, and with minimal inconvenience to a patient, monitored externally.

SUMMARY OF THE INVENTION

According to one aspect the present invention comprises a system for measuring the response of a neural system to stimulation by an auditory prosthesis, wherein selected stimulus electrodes provide an electrical stimulus, and after a predetermined period a potential is detected across a selected sense pair of electrodes, said potential being indicative of at least one parameter of response by said neural system.

Preferably after said electrical stimulus, all electrodes are open circuited for a predetermined period prior to said potential being detected. Preferably the system includes an amplifier and means for nulling said amplifier. Preferably said means for nulling nulls said amplifier during said predetermined period. Preferably said means for nulling comprises a plurality of cascaded gain stages, adapted at the end of said period to release said stages sequentially such that any offset voltage is substantially cancelled.

Preferably the stimulus electrodes are different to the sensing electrodes.

Preferably the auditory prosthesis is a cochlear prosthesis. Preferably the response measured is the evoked action potential of the auditory nerve.

Preferably said cochlear prosthesis includes an array of electrodes including both intra-cochlear and extra-cochlear electrodes.

According to a further aspect the invention comprises a telemetry system for measuring the response of a neural system to stimulus by an auditory prosthesis, wherein said auditory prosthesis includes a electrode array, said array being used for stimulation and to sense said response.

Preferably said measurement occurs a predetermined time after stimulation has occurred.

Preferably after electrical stimulation, all electrodes are open circuited for a predetermined period prior to said response being detected.

Preferably the auditory prosthesis is a cochlear prosthesis. Preferably the response measured is the evoked action potential of the auditory nerve.

Preferably said cochlear prosthesis includes an array of electrodes including both intra-cochlear and extra-cochlear electrodes.

Preferably the stimulus electrodes are different to the sensing electrodes.

According to another aspect the present invention comprises an implantable auditory prosthesis, comprising an intra-cochlear electrode array, and at least one extra-cochlear electrode.

According to the present invention, it has been discovered that a most effective way of measuring response to neural stimulation, particularly for measuring evoked auditory potential but also applicable to other stimulation regimes, is to use the stimulus array itself to receive the response. To enable this to operate effectively, the electrodes of the stimulus array are preferably open circuited for a period, after which the induced response may be measured. This removes any requirement for additional separate measurement sensors to be implanted. In a multi-electrode array such as is generally utilised in a cochlear implant, different electrode pairs are preferably used for stimulus and measurement.

BRIEF DESCRIPTION OF DRAWINGS

The invention will now be described in more detail with reference to the drawings, in which.

DETAILED DESCRIPTION

Figure 1:
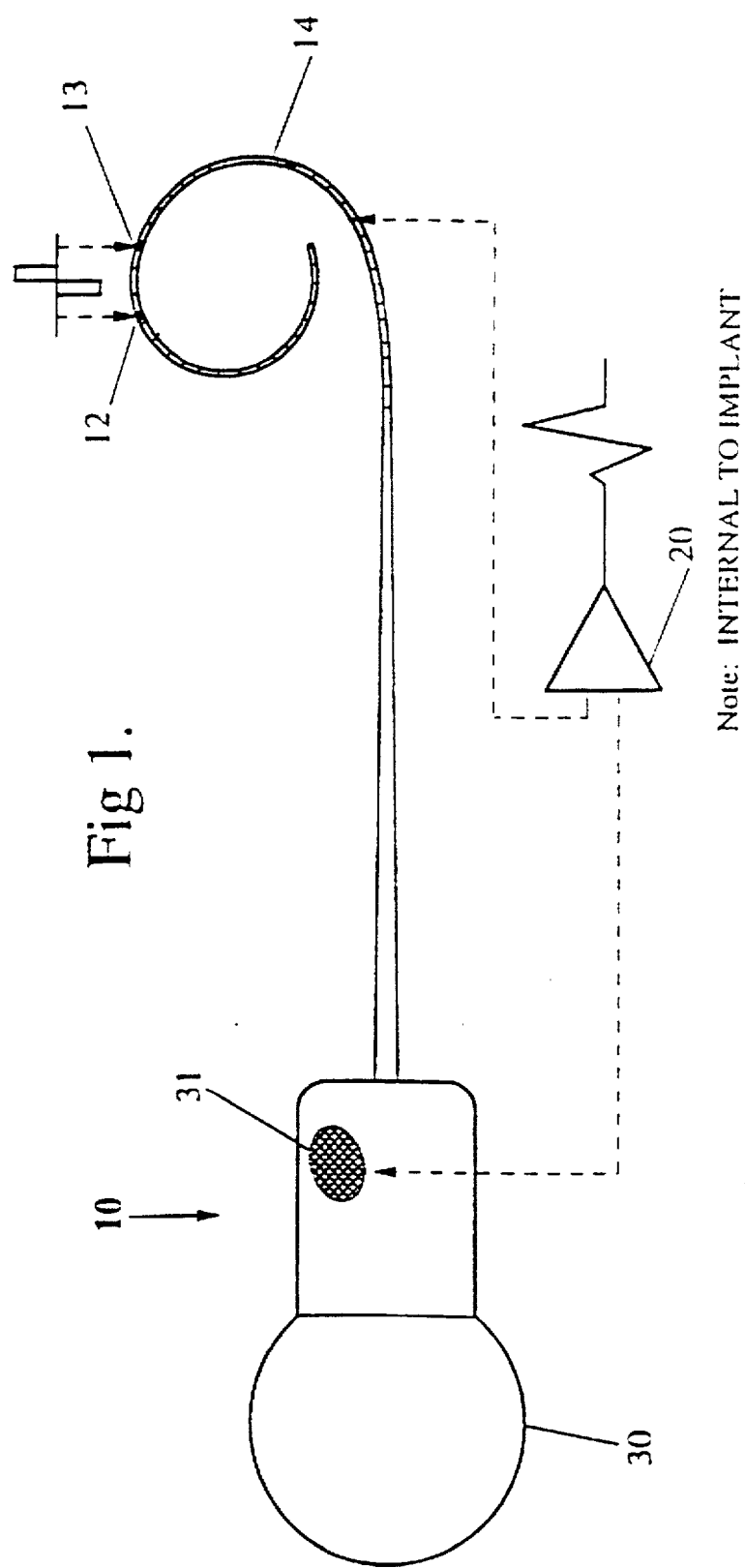
FIG. 1 illustrates the general arrangement of the inventive system.

Referring to FIG. 1, it is initially noted that the electrode array 10 is used both for stimulating, and for detecting the evoked response. Detected data is transmitted via the RF link already provided for transmitting power and data to the implant 10.

It will be noted that the implant, in addition to the intra-cochlear electrodes, preferably includes one or more extra-cochlear electrodes 31. For the telemetry of evoked neural potentials, it is greatly preferred to use different electrodes for delivering the stimulus, and for sensing the evoked action potential of the auditory nerve (EAP). Thus, for monopolar stimulation and measurement, one extra-cochlear electrode may be used for stimulating, and the other for sensing.

The EAP may according to the present invention be measured across any two sense electrodes. The waveform on the sense electrodes consists of the EAP nerve response plus the stimulus artefact. The stimulus artefact is decaying exponentially, but can in many cases be orders of magnitude larger than the nerve response itself. The electrode pair chosen will optimally detect maximum EAP gradient, and minimum stimulus artefact. The illustrative sense pair with reference to FIG. 1 uses intra-cochlear electrode 14 and extra-cochlear electrode 31.

Similarly, the stimulus pair 12, 13 may be any selected electrode pair. The optimal sense pair may vary with the stimulus pair selected, and may vary from patient to patient, as would be understood by those skilled in the art. Whilst it is preferred that the sense electrode pair be distinct from the stimulating electrode pair, the present invention encompasses the use of the same electrodes or electrode pair.

The sense pair potential difference is amplified by a suitable amplifier 20 to produce (ultimately) an EAP measurement on apparatus external to the patient. The amplified signal is sampled at 16 intervals and transmitted via the RF link, each sample being a pair of pulses with a pulse separation proportional to the amplifier output.

Figure 2:
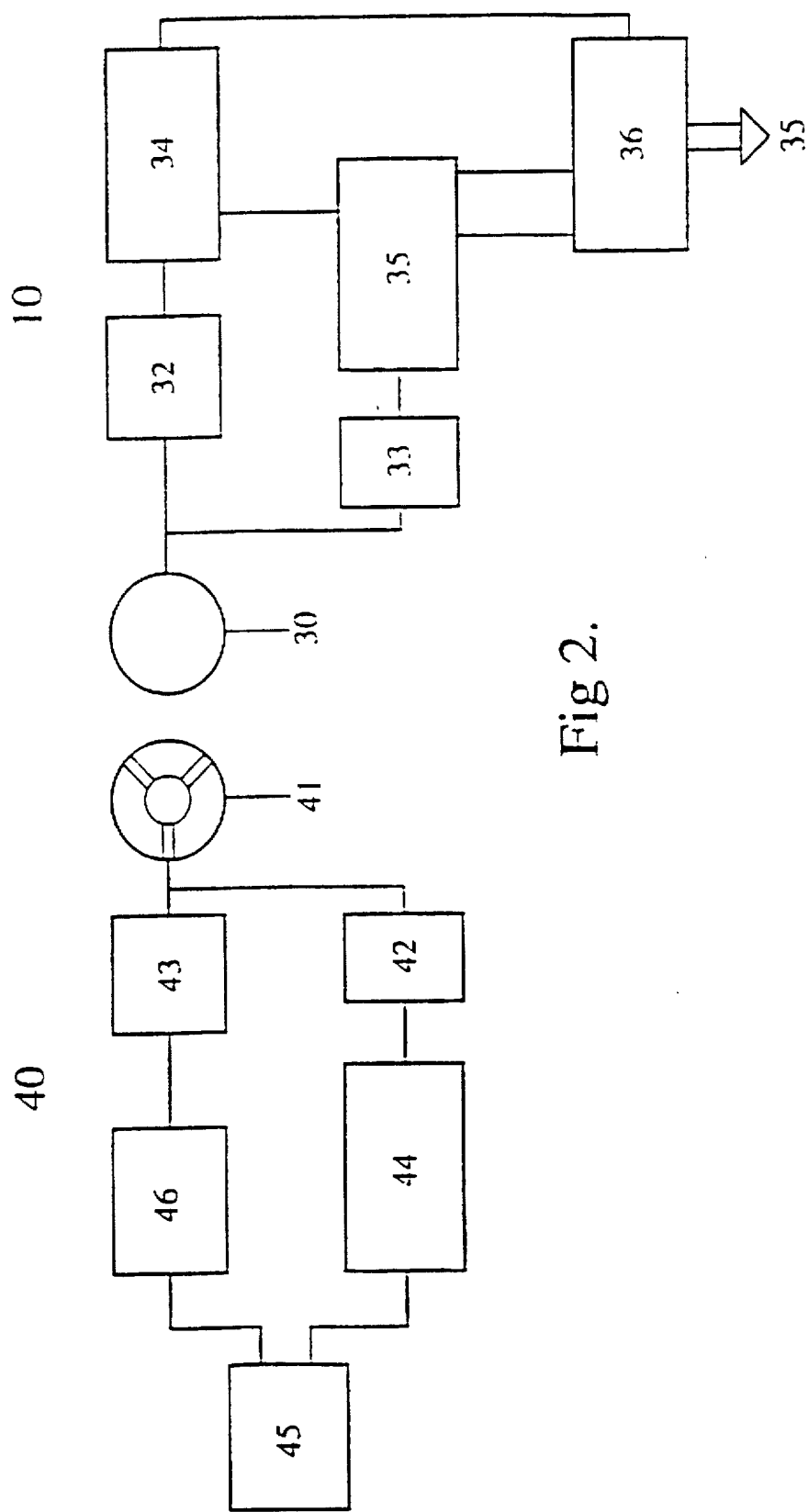
FIG. 2 is an overview in block form of the inventive system.

FIG. 2 illustrates in block form the internal and external aspects of the system.

Considering firstly the external system, the overall arrangement is controlled via digital processor 45, which may be a personal computer or similar device with suitable interfaces. Processor 45 drives the transmitter controller 46 and thus the transmitter stage 43 to send signals via RF link 41 to the implant 10. Transmitted telemetry data is received via RF link 41 passed through receiver 42 and comparator and timer/controller stage 44.

Commands are received in the implant 10 via RF link by receiver coil 30 and pass via receiver stage 32 to decoder/controller 34, which sends suitable commands to the EAP amplifier/telemetry controller 35 and to switch controller 36. Switch controller 36 controls the stimulation of selected pairs of electrodes. The sense electrode signal is amplified by EAP amplifier 40 and the telemetry controller processes the amplified signal for transmission via transmitter stage 33 and RF link 30 to the external system 40.

It will be appreciated that any suitable arrangement may be substituted for the precise arrangement outlined above. The overall technique for RF communication for powering and communicating with implanted devices is well known from, for example, commercially available devices manufactured by Cochlear Pty Ltd. However, the present invention should not be considered as limited to this mode of communication—the invention is independent of the communications mode, and could if desired be implemented in a directly connected system, for example. Preferably, the implanted system is integrated into a single chip as far as possible. Similarly, it will be apparent that with suitable modifications the present invention is applicable to other stimulation regimes and sites. The EAP application is used for the purposes of illustration.

Figure 3:
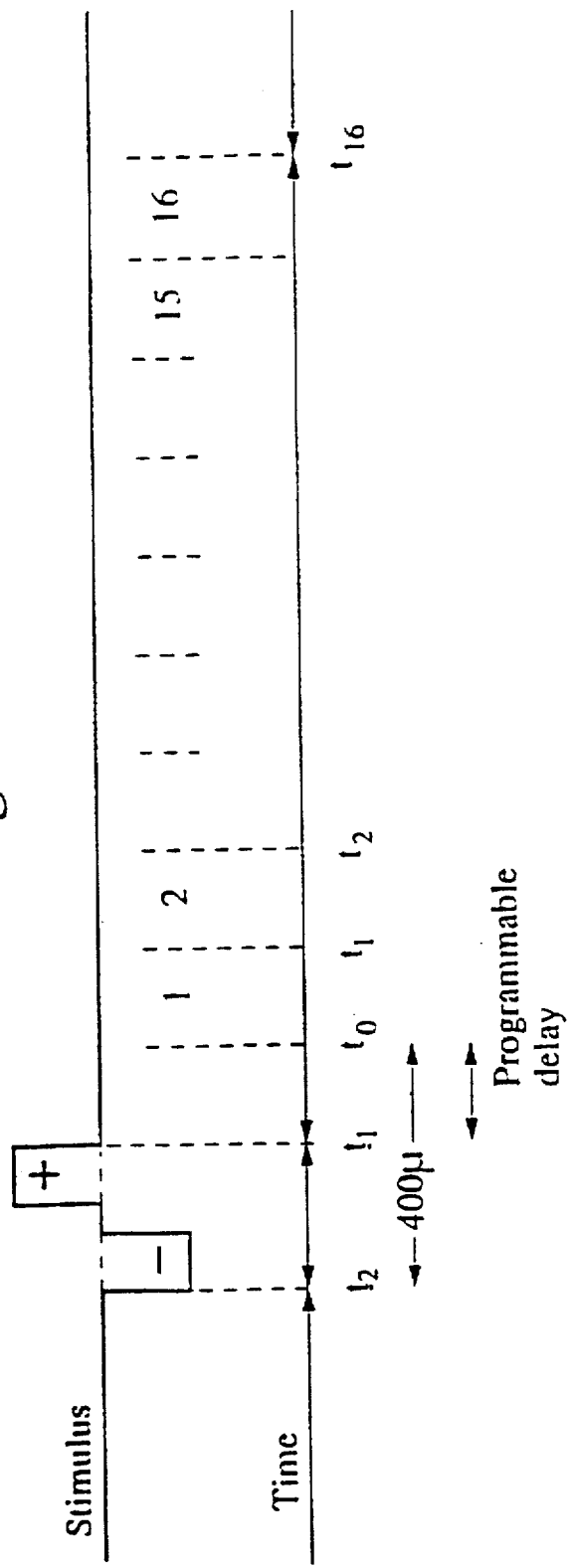
FIG. 3 is a timing diagram showing the stimulus and measurement sequence.

The operation of EAP detection according to the present invention can best be understood with reference to the timing diagram of FIG. 3. The top line illustrates stimulus via the stimulus electrode pair: the bottom represents time. In the preferred embodiment the all electrodes are short circuit prior to time $t_{-2}$ or stimulation.

At time $t_{-2}$, a stimulus pulse (illustratively a square biphasic pulse) is applied to stimulus pair 12, 13. Stimulus is completed at $t_{-1}$ and all electrodes (including the stimulus electrodes) are left open circuit. The amplifier 35 is nulled until time $t_0$. At time $t_0$ (for example), sampled measurements are taken at times $t_1, t_2 \ldots$ until time $t_{16}$. After $t_{16}$, the electrodes are again short circuited, ready for a further cycle of stimulus and EAP measurement. Note that short circuit before and after stimulus is one way of ensuring charge balance, but it is not necessary for recording the nerve response.

Preferably, the time between $t_{-2}$ and $t_0$ is about or slightly shorter than 400 μs, as this is a typical time between stimulus onset and nerve response occurrence. Of course, this may be varied as is appropriate for a given application. The period between $t_{-1}$, and $t_0$ is preferably programmable such that the nulling period ends just before the expected EAP occurrence, thereby minimising the detection of stimulus artefacts. This programmable delay is controlled by the telemetry controller 35.

Open circuiting all electrodes (including the stimulus electrodes after stimulation) further reduces the stimulus artefact and the required dynamic range of the amplifier. This arrangement has a further advantage in that one of the sense electrodes can be connected to the common supply rail and a single ended amplifier can be used. If preferred, a fully differential input stage could be used instead of the single ended amplifier.

The sample intervals are typically 100 μs, hence the sampling window is 1.5 to 2.0 ms. Both programmable delay time and the sampling period can be adjusted over a wide range to optimise the position and duration of the measurement window. This also allows recording of nerve responses other than the auditory response which result from the stimulus.

The measurement sequence is preferably repeated several times and averaged to further increase the signal to noise ratio of the measurement. The recorded signal required further post processing to eliminate the stimulus artefact from the composite signal. This could involve techniques known in this art such as masking stimulus and alternate phase sequences.

Figure 4:
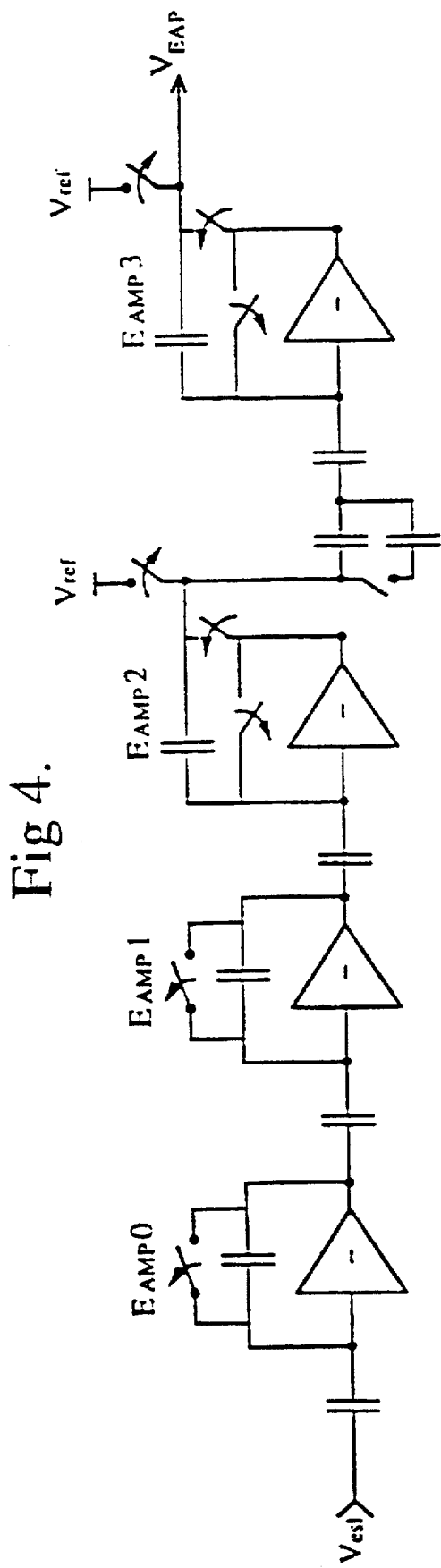
FIG. 4 is a schematic diagram showing one circuit arrangement for the preferred amplifier arrangement according to the present invention.

FIG. 4 illustrates a preferred implementation of the amplifier using four cascaded single-ended gain stages AMP0, AMP1, AMP2, AMP3. Illustratively, each stage has a gain of 20 dB. Any suitable amplifier design may be used for individual gain stages, as would be well understood by those skilled in the art. All amplifiers are preferably nulled before the recording period (initial delay) and any offset voltage is stored on the input capacitors. The length of the nulling period is programmable and controlled by telemetry controller 35.

At the end of the nulling period (FIG. 3,$t_0$) the amplifier stages are released sequentially, so as to compensate for offset voltage due to the charge injection into the previous stage.

It can be seen from FIG. 4 that $AMP_0$ and $AMP_1$ have a self-biased DC offset, while $AMP_2$ and $AMP_3$ are biased around $V_{ref}$ which is approximately half way between the supply rails, so that the output range is optimised. The last 2 stages have switchable gain of 20 dB or 0 dB, and as a result the amplifier may be set for gain of 40,60 or 80 dB.

This arrangement allows for accurate measurement of $V_{EAP}$, without the necessity to separately compensate or adjust for offsets.

It will be appreciated that variations and additions are possible within the spirit and scope of the invention.

We claim:

1. A cochlear implant for implantation into a patient for stimulating the patient's aural nerve, comprising:

a receiver receiving control signals including ambient signals indicative of ambient noise;

a plurality of electrodes, at least some of which are adapted to extend into the cochlea of the patient;

a controller for applying stimulation signals corresponding to said control signals to said electrodes;

a sensor coupled to said electrodes for sensing a sensed signal indicative of a response of said aural nerve to said stimulation signals a predetermined time after said stimulation signals are applied, said sensed signals being indicative of a parameter of response of the patient's neural system; and a measuring device for measuring said response;

wherein said controller open circuits said electrodes after said stimulation signals are applied.

2. The measuring system of claim 1 wherein said plurality includes stimulus electrodes and sense electrodes, said stimulus electrodes being different than said sense electrodes.

3. The measuring system of claim 1 wherein said array includes intra-cochlear and extra-cochlear electrodes.

4. The measuring system of claim 1 wherein said sensor includes an amplifier and means for nulling said amplifier.

5. The measuring system of claim 4 wherein said means for nulling nulls said amplifier during said predetermined period.

6. The measuring system of claim 4 wherein means for nulling comprises a plurality of gain stages, said means for nulling being adapted to release said stages sequentially at the end of said predetermined period so that any offset voltage is substantially canceled.

7. A cochlear prothesis for stimulating a neural system, said prosthesis comprising:

a source for a stimulus;

a plurality of electrodes coupled to said source, at least some of said electrodes being arranged to deliver said stimulus to said neural system, said plurality of electrodes including a pair of sense electrodes;

a controller for applying said stimulus to said plurality of electrodes and for open circuiting said plurality of electrodes for a predetermined period after said stimulus is applied; and a sensor for detecting a response on said pair of sense electrodes, said response being indicative of a reaction of said neural system to said stimulus.

8. The prosthesis of claim 7 wherein said stimulus is delivered to an auditory nerve and said response is an evoked potential of said auditory nerve.

9. The prosthesis of claim 7 wherein said plurality electrodes includes stimulating electrodes for delivering said stimulus.

10. The prosthesis of claim 9 wherein said stimulating electrodes are separate from said pair of sense electrodes.

11. The prosthesis of claim 7 wherein said plurality of electrodes includes intra-cochlear and extra-cochlear electrodes.

* * * * *